United States Patent

Hermann et al.

(10) Patent No.: US 7,473,913 B2
(45) Date of Patent: Jan. 6, 2009

(54) GANTRY SYSTEM FOR A PARTICLE THERAPY FACILITY

(75) Inventors: Klaus Hermann, Nürnberg (DE);
Werner Kaiser, Langquaid (DE);
Andres Sommer, Langensendelbach (DE); Torsten Zeuner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 334 days.

(21) Appl. No.: 11/499,825

(22) Filed: Aug. 4, 2006

(65) Prior Publication Data

US 2007/0029510 A1   Feb. 8, 2007

Related U.S. Application Data

(60) Provisional application No. 60/705,824, filed on Aug. 5, 2005.

(30) Foreign Application Priority Data

Aug. 5, 2005   (DE) .................. 10 2005 037 018

(51) Int. Cl.
*G21K 5/10* (2006.01)
*H01J 37/30* (2006.01)

(52) U.S. Cl. .................. 250/492.3; 600/407; 600/1

(58) Field of Classification Search ........... 250/492.3, 250/491.1; 600/407, 1
See application file for complete search history.

(56) References Cited

U.S. PATENT DOCUMENTS

| 6,385,288 | B1 | 5/2002 | Kanematsu |
| 7,193,227 | B2* | 3/2007 | Hiramoto et al. ......... 250/492.3 |
| 2004/0024300 | A1 | 2/2004 | Graf |
| 2004/0113099 | A1 | 6/2004 | Eickhoff et al. |
| 2004/0227104 | A1* | 11/2004 | Matsuda et al. ......... 250/492.1 |
| 2007/0284548 | A1* | 12/2007 | Kaiser et al. ............. 250/522.1 |

FOREIGN PATENT DOCUMENTS

| EP | 1 396 278 A2 | 3/2004 |
| EP | 1 402 923 A1 | 3/2004 |
| EP | 1 479 411 B1 | 4/2005 |
| WO | WO 00/74779 A1 | 12/2000 |

OTHER PUBLICATIONS

Stefan Reimoser, "Development and Engineering Design of a Novel Exocentric Carbon-Ion Gantry for Cancer Therapy (The "Riesenrad" Gantry)", Dissertation, Genf, Oct. 2000, pp. 28-33.

* cited by examiner

*Primary Examiner*—Jack I Berman

(57) ABSTRACT

The invention relates to a gantry system for a particle therapy facility, having a beam guidance gantry which has elements for beam guidance, and having a measurement gantry which has a device for beam monitoring. The measurement gantry and beam guidance gantry are thus of a mutually independent design and are, in particular, arranged in a mutually concentric manner. A gantry system of this kind is inter alia less susceptible to mechanical deviations during rotation of the beam guidance gantry.

14 Claims, 2 Drawing Sheets

GANTRY SYSTEM FOR A PARTICLE THERAPY FACILITY

CROSS REFERENCE TO RELATED APPLICATIONS

The present application claims the benefit of the provisional patent application filed on Aug. 5, 2005, and assigned application No. 60/705,824. The present application also claims priority of German application No. 10 2005 037 018.7 filed on Aug. 5, 2005. Both of the applications are incorporated by reference herein in their entirety.

FIELD OF THE INVENTION

The invention relates to a gantry system for a particle therapy facility, having a beam guidance gantry which has elements for beam guidance.

BACKGROUND OF THE INVENTION

In particle therapy, gantry systems are used to irradiate patients from different directions with particles, that is to say protons, carbon ions or oxygen ions, for example. For this purpose the gantry comprises a plurality of deflection magnets which rotate about the axis of rotation of the gantry system. Beam monitoring elements are usually arranged at a beam exit. These elements supply, for example, information concerning the site and intensity of the particle beam and are used for the output of controlled variables which notify a control system of the site and number of particles administered and of the amount of energy used. This is necessary especially in the case of radiation therapy using a scan system, since here the proton beam scans over the tissue to be irradiated in the form of what is called a pencil beam. Examples of gantry systems are known, for example, from EP 1 396 278 A2, EP 1 479 411 B1 and EP 1 402 923 A1.

In known gantry arrangements the particle beam is directed onto a stationary treatment target known as the isocenter. The irradiation angle can be freely adjusted such that a patient awaiting treatment can be irradiated from different directions in the same treatment position. Owing to the high particle energies of some 100 MeV, correspondingly large deflection magnets are required for beam guidance. These magnets are arranged on a frame and can rotate on circular paths with relatively large radii of, for example, some meters about an axis of rotation which extends through the isocenter. The problem thus arises, in particular, that the gantry system, which has been dimensioned with a view to adequate rigidity, nevertheless, depending on the angle of rotation, undergoes different displacements or distortions or deformations such that, for example, the positions of the deflection and beam-forming magnets vary. This has a disadvantageous effect on precision during guidance of the particle beam and thus on accuracy of aim and reproducibility.

The problem of the considerable structural dead weight has a heightened effect in the case of gantry systems for heavy ions (carbon ions), since here the magnets and the beam guidance elements arranged between the magnets are substantially heavier.

SUMMARY OF THE INVENTION

An object of the invention is to provide a gantry system which enables accurate radiation therapy to be administered irrespective of the displacements or distortions or deformations of the gantry.

This object is achieved as claimed in the invention by virtue of a gantry system for a particle therapy facility as claimed in the independent claim, which system comprises a beam guidance gantry which has elements for beam guidance, and a measurement gantry which has a device for beam monitoring. The device thus measures at least one beam parameter of the administered beam, the beam parameter being provided for control of the particle therapy facility.

The device for the output of the parameter is preferably provided on a control system of the particle therapy facility. As part of the beam monitoring apparatus, the device can thereby provide feedback for the administration of radiation therapy.

For an irradiation procedure the measurement gantry is preferably first rotated into an angular position intended to form the basis for the radiation therapy. In this position, a measuring unit of the device for measuring particles is then exposed to radiation after the beam guidance gantry has been correspondingly rotated. This enables beam parameters, in particular the site and/or the energy and/or the number of administered particles of the beam to be measured.

One advantage of an embodiment of the invention is that the effects of displacements or distortions or deformations caused by the weight load of the beam guidance elements such as deflection magnets or quadrupole magnets were restricted to the beam guidance gantry. The measurement gantry, which is of a stand-alone and substantially lighter and smaller design, is, by contrast, not subjected to stress and distorted. This has the further advantage that the device for beam monitoring can be positioned very accurately relative to the isocenter independently of the beam guidance gantry.

A further advantage is that, owing to the smaller mass, the measurement gantry can be positioned more quickly and more accurately. If the measurement gantry is also arranged inside the beam guidance gantry, rotation of the beam guidance gantry does not put at risk a patient and/or operating personnel located inside the measurement gantry. It is thus possible for patient positioning, for example, and, if the measurement gantry also has an imaging device, position verification to be started without, at that time, the beam guidance gantry already being rotated into the angular position later required. If the measurement gantry also comprises a laser system for patient positioning and/or an imaging position verification system, etc. as already mentioned above, these systems are also independent of the angle of rotation, that is to say, they supply information that is not conditional on the position of the beam guidance gantry.

A further advantage relating to the beam guidance gantry is that said gantry becomes less expensive since the positioning accuracy and any positioning errors can be corrected by the independently arranged beam monitoring apparatus.

A further advantage is that the measurement gantry and beam guidance gantry can be designed independently in respect of energy supply, signal processing and the installation of components.

A further advantage is that all the enclosures visible in a patient room can be fitted on the measurement gantry.

In an advantageous embodiment of the gantry system, the measurement gantry comprises apparatus for verifying the patient's position and/or a patient positioning device and/or a laser positioning device. The patient's position is verified shortly before exposure to radiation with, for example, the aid of pairs of x-ray sources and x-ray detectors arranged at an angle. A patient positioning device comprises, for example, a video camera system which matches the patient's position to a required position. A laser positioning device comprises, for example, a laser cross formed by a plurality of laser beams.

An advantage of such embodiments is that an imaging device can be positioned more quickly relative to the patient for patient position verification, since the rotation of the measurement gantry with the imaging devices is independent of the rotation of the beam guidance gantry. A further advantage is the fact that, during the imaging process, the drive and bearing of the beam guidance gantry are not under stress. The independent rotatability of the measurement gantry also, for example, permits orthogonal imaging relative to the irradiation angle. In the case of a continuous, rapid rotation of the measurement gantry, said independent rotatability also permits the capture, from different angles, of a plurality of fluoroscopic images from which, for example, 3D image data sets can be obtained for matching with CT position planning data.

In further embodiments of the gantry system, the measurement gantry and the beam guidance gantry can be installed independently of each other and/or they can be adjusted in their angular position independently of each other and/or they are mechanically, thermally and/or vibrationally separate.

Further advantageous embodiments of the invention are characterized by the features of the subclaims.

BRIEF DESCRIPTION OF THE DRAWINGS

An explanation follows of two exemplary embodiments of the invention with reference to FIGS. 1 to 3, in which.

DETAILED DESCRIPTION OF THE INVENTION

Figure 1:
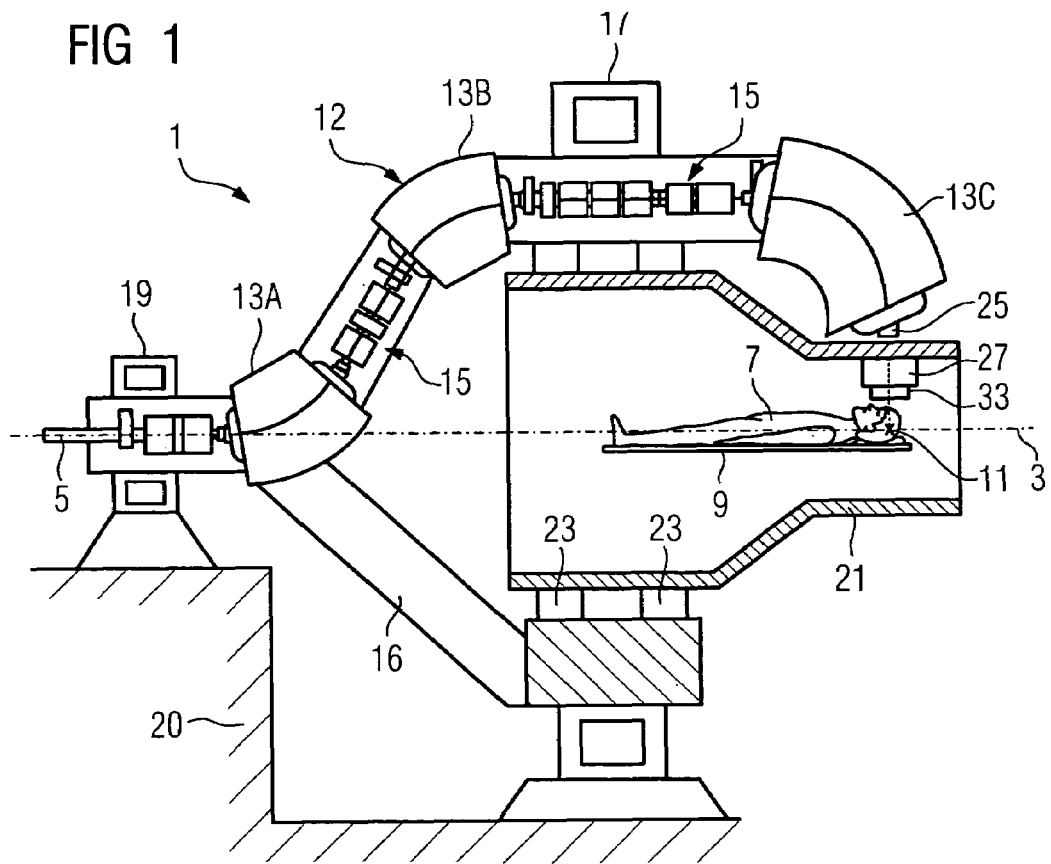
FIG. 1 is a diagrammatic representation of a first embodiment of a concentric gantry system in a vertical sectional drawing through its axis of rotation.

FIG. 1 shows a gantry system 1 in a vertical sectional drawing along an axis of rotation 3. The object of the gantry system 1 is to be able to guide a particle beam 5 such that a patient 7 having tissue that is to be irradiated, for example having a brain tumor, can undergo radiation therapy from any direction of incidence. For this purpose, the patient 7 is positioned, for example on a patient bed 9, with the tissue to be irradiated in an isocenter 11 of the gantry system 1. The isocenter 11 preferably lies on the axis of rotation 3. The direction of incidence can be at any angle to the axis of rotation 3. For illustrative purposes, an angle of 90° was selected in FIG. 1. When the gantry system 1 rotates, the direction of incidence rotates about the axis of rotation 3.

In the exemplary embodiment shown in FIG. 1, the particle beam is guided by the beam guidance gantry 12 from the beam entry into the gantry system 1 to the patient 7. The particle beam 5 enters the gantry system 1 on the axis of rotation 3. The particle beam 5 is deflected from the axis of rotation 3 by a first deflection magnet 13A before it is deflected by further deflection magnets 13B and 13C such that it passes, for example, radially through the isocenter 11. Further beam guidance elements 15, for example quadrupole magnets, raster scan magnets, etc. are arranged between the deflection magnets 13A, 13B, 13C. The deflection magnets 13A, 13B, 13C and the beam guidance elements 15, together with a support structure 16, form the beam guidance gantry 12. A bearing device is used for rotation of the beam guidance gantry 12. The bearing device comprises a first bearing 17 which is arranged in an axial direction, where possible at the level of the centre of gravity of the beam guidance gantry 12, and also comprises a bearing 19 which is arranged in the region of the beam incoupling. The bearings 17 and 19 are supported on a base 20. The bearing 17 is preferably in the form of a bearing ring.

Owing to the weight of the beam guidance gantry there is the possibility of distortions which cannot be completely prevented even by a very rigidly designed support structure 16 and which lead to positional variations, for example of the beam guidance elements 15, and thus to beam displacement.

Arranged concentrically with the beam guidance gantry 12 inside the beam guidance gantry 12 is a measurement gantry 21. The measurement gantry 21 can rotate independently of the beam guidance gantry 12. This is made possible by bearings 23, which are arranged in the direction of the axis of rotation at the level of the bearing 17 of the beam guidance gantry 12. The bearings 17 and 19 are supported on the base. The bearings 23 are likewise supported on the base 20, indirectly via the bearing 17.

In the region of the beam exit 25 of the beam guidance gantry, the measurement gantry 21 has a device 27 for beam monitoring. Apparatus for laser positioning and/or for patient position verification can also be fitted there. The weight of the measurement gantry 21 is much less overall, with the result that deformations depending on the angular position can be very largely prevented. The physical positions of the components supported by the measurement gantry are accordingly reproducible, that is to say, for example the distance to the isocenter 11 is not dependent on the angle of rotation.

The device 27 for beam monitoring measures at least one beam parameter of the administered beam, for example the beam position, the beam intensity and/or the beam energy; the beam parameter or parameters are provided for control of the particle therapy facility and are thus an essential constituent in the administration of radiation therapy. The beam guidance gantry and the measurement gantry thus cooperate during radiation therapy in order to administer a beam with the appropriate parameters. The measurement gantry enables the administered dose and the position of the administered beam to be actively measured. The feedback of this information to, for example, a control unit of the particle therapy facility is required for the irradiation procedure so that, for example, the desired dose can be administered very precisely. This measurement of "primary" parameters of the beam differs from the measurement of radioactive secondary products, for example with a PET machine which, following administration, supplies information concerning the site of the administered dose and cannot be used for control of the particle therapy facility. This latter machine is used far more for quality assurance than for the controlled administration of the irradiation procedure.

The gantry system 1 is preferably designed so that, for radiation therapy, the measurement gantry 21 can be rotated into an angular position in which a measuring unit of the device is penetrated by the particle beam when the beam guidance gantry 12 is correspondingly rotated, in order to measure, in particular, the site and/or the energy and/or the number of administered particles of the beam.

Accordingly, the measuring unit of the device 27 has, for example, a location detector (e.g. multichannel plates) for defining position and/or a dosimeter for measuring intensity.

Figure 2:
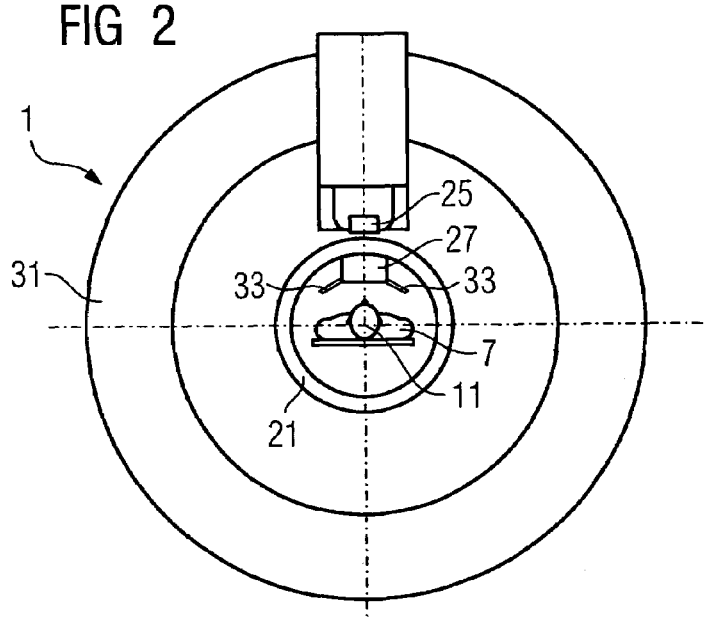
FIG. 2 is a front view of the gantry in FIG. 1.

To illustrate the structure in FIG. 1, reference is made to FIG. 2, which is a front view of the gantry system 1 in the direction of the axis of rotation. Visible there are the patient 7 in the isocenter 11 of the gantry system 1, the beam exit 25 and an outer gantry ring 31 of the beam guidance gantry 12, as well as the measurement gantry 21 arranged therein with the device 27 for beam monitoring. Also visible there are two flat panel detectors 33, which are arranged on both sides of the device 27 for beam monitoring and are used for position verification. The x-ray sources required for this purpose are located opposite the patient and are integrated into the measurement gantry 21 and not visible in FIG. 2.

Figure 3:
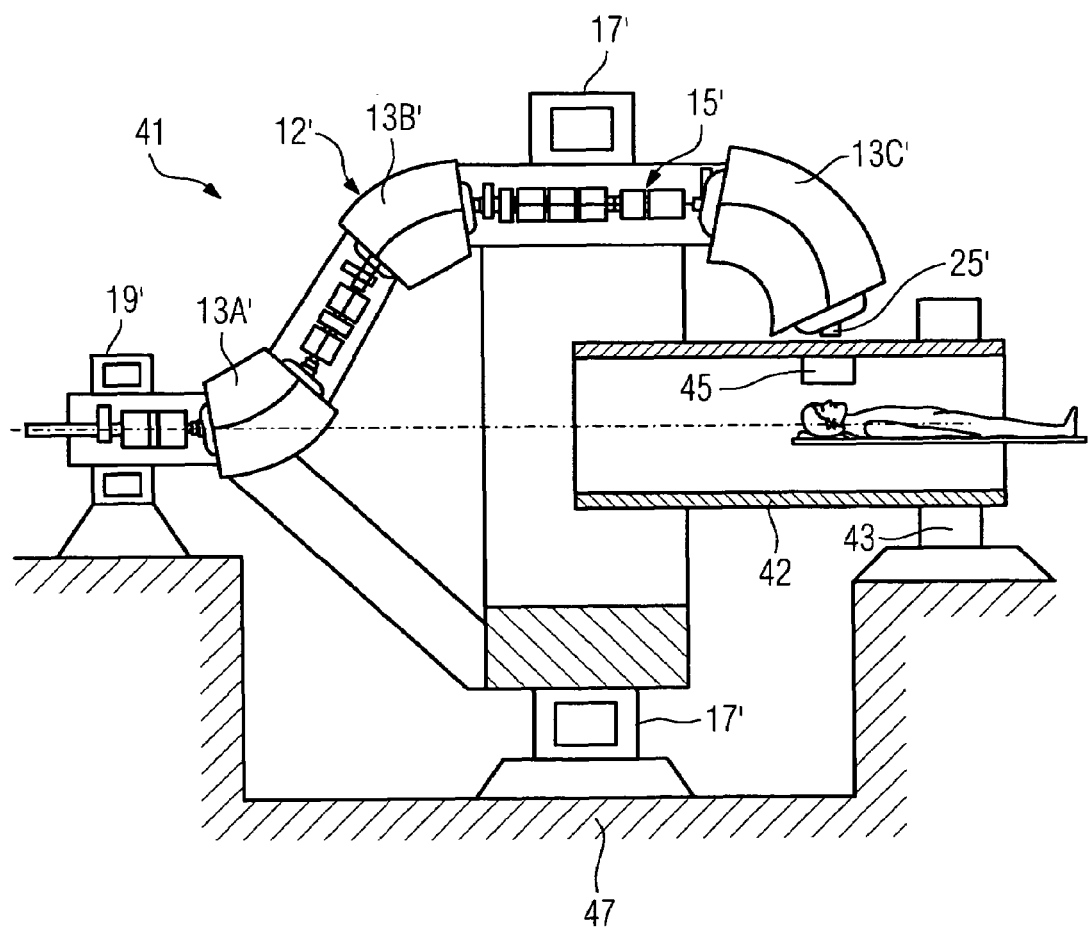
FIG. 3 is a diagrammatic representation of a second embodiment of a concentric gantry system in a vertical sectional drawing through its axis of rotation.

FIG. 3 shows a further exemplary embodiment of a concentric gantry system 41, the beam guidance gantry 12' having the components referred to in FIG. 1, for example deflection magnets 13A', 13B', 13C', bearings 17' and 19', beam exit 25', etc.

Unlike the embodiment shown in FIG. 1, a measurement gantry 42 is not supported indirectly via the beam guidance gantry 12'. Instead there is provided a bearing 43 which is itself arranged on a base 47 of the particle therapy facility. The bearing 43 and the bearings 17' and 19' are thus mechanically separate. This embodiment facilitates complete mechanical, thermal and/or vibrational separation of the measurement gantry and beam guidance gantry 12' and 42. The measurement gantry 42 again comprises means 45 for imaging, beam monitoring and/or laser positioning.

The invention claimed is:

1. A gantry system for a particle therapy facility, comprising:
   a beam guidance gantry comprising a beam guidance element; and
   a measurement gantry comprising a device for beam monitoring and measuring a beam parameter which controls the particle therapy facility.

2. The gantry system as claimed in claim 1, wherein a device for outputting the beam parameter is provided on a control system of the particle therapy facility.

3. The gantry system as claimed claim 1, wherein the measurement gantry is rotated into an angular position and a measuring unit of the device is penetrated by a particle beam from the beam guidance gantry rotated at the identical angular position in order to measure the beam parameter.

4. The gantry system as claimed claim 3, wherein the beam parameter is selected from the group consisting of: a site, energy, and a number of particles of the beam.

5. The gantry system as claimed claim 3, wherein the measuring unit comprises a location detector for detecting a position or a dosimeter for measuring an intensity of the particle beam.

6. The gantry system as claimed claim 1, wherein the measurement gantry comprises an apparatus for verifying a position of a patient, a patient positioning device, or a laser positioning device.

7. The gantry system as claimed claim 1, wherein the measurement gantry and the beam guidance gantry are independent of each other in installation, adjustment, energy supply, or signal processing.

8. The gantry system as claimed claim 1, wherein the measurement gantry and the beam guidance gantry are mechanically separated.

9. The gantry system as claimed claim 1, wherein the measurement gantry and the beam guidance gantry are thermally or vibrationally separated.

10. The gantry system as claimed claim 1, wherein the measurement gantry is arranged concentrically with the beam guidance gantry and inside of the beam guidance gantry.

11. The gantry system as claimed claim 1, wherein the beam guidance gantry is rotatably arranged on a bearing device and the measurement gantry is rotatably arranged on a measurement gantry bearing device which permit an independent rotation of the beam guidance gantry and measurement gantry.

12. The gantry system as claimed in claim 11, wherein the bearing device is supported on a base and the measurement gantry bearing device is arranged radially inside the bearing device and indirectly supported on the base via the bearing device.

13. The gantry system as claimed in claim 11, wherein the bearing device and the measurement gantry bearing device are independently supported on a base.

14. The gantry system as claimed in claim 13, wherein the measurement gantry bearing device is supported on a side of the beam guidance gantry which is opposite to a delivery direction of the particle beam into the beam guidance gantry.

* * * * *